(12) United States Patent
Aller

(10) Patent No.: US 6,479,241 B1
(45) Date of Patent: Nov. 12, 2002

(54) HIGH THROUGHPUT SCREENING OF THE EFFECTS OF ANTI-CANCER AGENTS ON EXPRESSION OF CANCER RELATED GENES IN VARIOUS CELL LINES

(75) Inventor: Alex Aller, Hoover, AL (US)

(73) Assignee: Southern Research Institute, Birmingham, AL (US)

( * ) Notice: Subject to any disclaimer, the term of this patent is extended or adjusted under 35 U.S.C. 154(b) by 0 days.

(21) Appl. No.: 09/657,535

(22) Filed: Sep. 8, 2000

Related U.S. Application Data

(60) Provisional application No. 60/153,036, filed on Sep. 10, 1999.

(51) Int. Cl.[7] .......................... C12Q 1/68; C12P 19/34; C12N 5/00; C12N 5/06; C07H 21/04
(52) U.S. Cl. .................... 435/6; 435/69.1; 435/91.1; 435/91.2; 435/325; 435/344; 536/24.3; 536/24.33; 536/23.1
(58) Field of Search ..................... 435/6, 69.1, 344, 435/325, 244, 91.1, 91.2; 536/24.3, 24.33, 24.32, 23.1; 424/9.2

(56) References Cited

U.S. PATENT DOCUMENTS

| | | | | |
|---|---|---|---|---|
| 5,912,356 A | * | 6/1999 | Townsend et al. | 548/304.4 |
| 5,976,793 A | * | 11/1999 | Foulkes et al. | 435/6 |
| 6,159,693 A | * | 12/2000 | Shultz et al. | 435/6 |

OTHER PUBLICATIONS

Riss et al. High Throughput Screening for Cytotoxicity Using the CellTiter 96 A Queous One Solution Assay. Promega Notes No. 69, p. 1–5, Dec. 1998.*

Halliday et al. Development of a Moderate Throughput Assay Using TaqMan PCR Technology to Identify Inhibitors of B. virus. Antiviral Research, vol. 37, Issue 3, p. A66, Abstract 96, Mar. 1998.*

Morris et al. Rapid Reverse Transcription–PCR Detection of Hepatitis C Virus RNA in Serum by Using the TaqMan Fluorogenic Detection System. Journal of Clinical Microbiology, vol. 34, No. 12, pp. 2933–2936, Dec. 1996.*

Halliday et al. Development of a Moderate Throughput Assay Using TaqMan PCR Technology to Identify Inhibitors of B. virus. Antiviral Research, vol. 37, Issue 3, p. A66, Abstract 96.*

Eckert et al., "Potential of LightCycler technology for quantification of minimal residual disease in childhood acute lymphoblastic leukemia," Leukemia 14:316–323, 2000.

Bik–Yu Hui et al., "Detection of Multiple Gene Amplifications in Glioblastoma Multiforme Using Array–Based Comparative Genomic Hybridization," Laboratory Investigation 81(5):717–723, 2001.

Kallioniemi, "Biochip technologies in cancer research," Ann Med 33:142–147, 2001.

Kerr et al., "Analysis of Variance for Gene Expression Microarray Data," Journal of Computational Biology 7(6):819–837, 2000.

Khanna et al., Metastasis–associated Differences in Gene Expression in a Murine Model of Osteosarcoma,: Cancer Research 61:3750–3759, May 1, 2001.

Kreuzer et al., "LightCycler Technology for the Quantitation of bcr/abl Fusion Transcripts," Cancer Research 59:3171–3174, Jul. 1, 1999.

Mathiassen et al., "Tumor–associated antigens identified by mRNA expression profiling induce protective anti–tumor immunity," Eur. J. Immunol. 31:1239–1246, 2001.

Pinzani et al., "Type–2 somatostatin receptor mRNA levels in breast and colon cancer determined by a quantitative RT–PCR assay based on dual label fluorogenic probe and the TaqMan™ technology," Regulatory Peptides 99:79–86, 2001.

Tokunaga et al., "Application of Quantitative RT–PCR Using "TaqMan" Technology to Evaluate the Expression of CK 18 mRNA in Various Cell Lines," J. Exp. Clin. Cancer Res. 19(3):375–381, 2000.

\* cited by examiner

*Primary Examiner*—Gary Benzion
*Assistant Examiner*—Cynthia Wilder
(74) *Attorney, Agent, or Firm*—Rothwell, Figg, Ernst & Manbeck

(57) ABSTRACT

A high-throughput method for screening compounds for anticancer activity involves cultivating cells capable of expressing cancer genes in cell culture in microtiter plate wells in the presence of test compounds and detecting the level of gene expression by a quantitative nucleic acid amplification.

35 Claims, No Drawings

HIGH THROUGHPUT SCREENING OF THE EFFECTS OF ANTI-CANCER AGENTS ON EXPRESSION OF CANCER RELATED GENES IN VARIOUS CELL LINES

CROSS-REFERENCE TO RELATED APPLICATION

The present application is related to U.S. provisional patent application Ser. No. 60/153,036, filed on Sep. 10, 1999, which is incorporated herein by reference.

BACKGROUND OF THE INVENTION

The present invention relates to a high-throughput method for screening potentially active compounds which affect the expression of one or more mRNAs. More particularly, the invention relates to an in vitro mRNA expression method employing cell lines.

Most effective, specific anti-cancer drugs affect the expression of one or more mRNAs, and therefore proteins, in the cells that are the targets of these drugs. Analysis of the altered expression patterns of cell lines treated with a novel compound allows researchers to more accurately predict the effect a novel compound will have in vivo as well as determine which other drugs currently in use or development may be synergistic with the compound being analyzed. Furthermore, the analysis of a broad spectrum of mRNAs from cancer cells during exposure to anti-cancer agents allows scientists to more fully understand the molecular mechanism of action of novel anti-cancer agents. This understanding contributes to rational, molecular based drug design.

To date, the analysis of the altered expression pattern of even a single MRNA species over a time course and at different drug concentrations is a labor intensive and costly proposition. There has been a need for the development of a rapid methodology for analyzing altered MRNA expression of a large number of genes in a large number of cell lines in response to treatment of these cell lines with various concentrations of anti-cancer agents over an extended time course. This technology will allow quick and efficient analysis of the effect a novel agent has on expression of numerous mRNAs associated with apoptosis, signal transduction, cell proliferation, cellular differentiation and other cell functions associated with the ultimate effectiveness of an anticancer agent. This information will prove invaluable in predicting the efficacy of novel anticancer agents using in vivo models and in patients.

Although structure-function relationships and rational drug design have been successfully employed in research, a major component of such research still involves high-volume screening of large numbers of compounds. Accordingly, screening methods should be robust, sensitive, fast and capable of accommodating large numbers of samples simultaneously. In addition, experimental drugs often are available only in small quantities. A successful screening method therefore advantageously uses small cell culture volumes and sensitive detection methods. Currently, the standard 96-well microtiter plate format is preferred for these types of procedures.

SUMMARY OF THE INVENTION

In accordance with the present invention, a method for simultaneously screening a plurality of compounds for anti-tumor activity against a cell line involves the steps of:

(1) cultivating cells, which are capable of serving as targets for anticancer agents in culture medium in wells of a microtiter plate, each well containing a culture volume of from about 50 $\mu$L to about 200 $\mu$L;

(2) adding each compound being tested to separate cell-containing wells at a concentration at which the drug activity is to be tested;

(3) culturing the cells for a time sufficient for the cells to express target genes;

(4) subjecting a sample of cell lysate to quantitative nucleic acid amplification of a sequence from at least one target gene to determine the extent of expression for the target gene in each well; and (5) correlating the extent of gene expression, as determined by quantitative nucleic acid amplification, to the concentration of each compound to determine the effectiveness of the compounds in altering cellular gene expression.

It has been found that quantitative nucleic acid amplification provides a sensitive and reliable method for determining the extent of gene expression. The sensitivity of this detection method permits the use of very small cell numbers and culture volumes, in contrast to the relatively large culture volumes and conditions described in the prior art. The small culture volumes, in turn, permit the screening assay to be performed in a microtiter plate format and permit the use of very small amounts of test compounds. By using the microtiter plate format, numerous compounds can be tested simultaneously to provide a high-throughput screening method.

DETAILED DESCRIPTION OF THE INVENTION

The present invention relates to a high-throughput method for screening potentially active compounds which affect the expression of one or more mRNAs. The invention is a combination of robotics, standard molecular biology techniques (e.g., cell lysis, RNA isolation, reverse transcription), and real time PCR. The combination of these techniques yields a high throughput analysis that is unique. Preferably the methods are performed robotically in a clean environment using sterile disposables.

More particularly, the invention relates to an in vitro mRNA expression method employing cell lines. A method is described for screening compounds for antitumor activity by cultivating cells in small volumes in microtiter plates in the presence of test compounds and performing quantitative nucleic acid amplification of target genes to determine the effect of the test compound upon the expression of the genes. The advantage of this approach over current methodologies is that real time PCR allows accurate quantitation of the messages expressed in a cell population undergoing treatment with novel agents. It is generally accepted that anti-cancer agents may cause upregulation or downregulation in mRNA expression that may effect the ultimate outcome of treatment. Most genes are not turned completely on or completely off. It is this quantitatively altered expression pattern that is of interest in many cases. The use of this new technology will allow researchers to rapidly and accurately assess the changes in mRNA expression induced by novel anti-cancer compounds. Earlier technologies for performing such studies were manual methods of molecular biology. The advantage of the method disclosed here is the high speed capacity. This high speed capacity allows large scale molecular analysis which would not be feasible with manual methods.

It will be appreciated by those skilled in the art that the screening method described herein may be applied to a wide variety of genes. Such genes include, but are not limited to, the genes listed in Table I. Any cell line which can be cultivated in vitro can be employed in this method. Advantageously, the cells employed in the screening method express the genes that are associated with the condition being studied, e.g., a specific cancer gene, and which is a target for therapeutic interference. In addition to being used for screening for anticancer agents, other uses for the described method include analyzing cell lines for induction of apoptosis, analyzing cell lines for tubulin polymerization, analyzing cell lines for cell surface protein expression, analyzing cell lines for DNA damage such as loss of heterozygosity (LOH) and specific mutations via PCR, analyzing cell lines for cytotoxicity, and other similar uses as will be recognized by those of skill in the art.

TABLE I

Functional Categories of Genes

1) Cell growth and regulation

AIBC1
bax
bcl-2
Beta Catenin
BRCA1
CDIC-4
Cyclin D1
Cyclin E
c-abl
c-flk
c-fos
c-jun
c-kit
c-mpl
c-myc
E cadherin + gp78
EGFr
erb B2
FAA
fas
fas-ligand
gadd45
gadd153
GST
h-ras
Ki67
MDR1
MRP
NKX3
p21
p53
p110
PTEN
Telomerase
hTRT
VEGF
waf-1
ZAB C1

2) Apoptosis

Annexin V
Apaf-1
Bcl-2
Bcl-X
Bik
Mcl-1
Bak
Bad
Bax
PARP (Poly-ADP-Ribose-Polymerase)
Caspases-1
Caspases-2
Caspases-3
Caspases-4
Caspases-5
Caspases-6

TABLE I-continued

Functional Categories of Genes

Caspases-7
Caspases-8
Caspases-9
Caspases-10
Caspases-13
Caspases-14
Cytochrome C
c-IAP-1
d4-GD1
Daxx
DFF
DNase I
FADD
FAF1
Fas
1-FLICE
ICE
IkB
MEKK
Nc1-x1
NFkB
Rb
RIP
SGP-2
TNF-Rp55
TRADD
TRAF-3
TRAF-4
TRAIL 3) Oncogenes
4) Cell surface receptors/ligands
5) Adhesion molecules
6) Signal transduction molecules
7) Nuclear transcriptional regulators
8) DNA binding molecules
9) Glycolysis/gluconeogenesis molecules
10) DNA repair enzymes The cells may be cultured by techniques well known to those skilled in the art. The cells are cultivated in a nutrient medium that supports cell viability and growth. While the medium may vary, depending upon the particular cells employed, suitable media include Dulbecco's modified Eagle's medium ("DMEM") or Roswell Park Memorial Institute medium (RPMI-1640) supplemented with 10% fetal bovine serum. Culture plates are advantageously maintained in humidified incubation chambers at 37° C. in an atmosphere containing 5% carbon dioxide.

Cell-containing media are added to the wells of a microtiter plate. A preferred format for carrying out the screening method of this invention utilizes a conventional 96-well microtiter plate. Each well contains less than about 200 $\mu$L, preferably less than about 100 $\mu$L of culture medium, e.g., from about 50 $\mu$L to about 100 $\mu$L of culture medium. When using the 96-well microtiter plate format, it is preferred to use only the internal wells for testing, because of "edge effects" caused by evaporation of media from the outer wells. Accordingly, the outer rows and columns of wells are advantageously filled with media only.

Once plated in the wells, the cells are cultivated to a desired cell density. When the cell growth has reached the desired density, the compounds to be tested are added to the microtiter plate wells. It is preferred that each compound being tested be added to a plurality of wells at different concentrations. It is usually desired that the compound be added in dilutions that include a useful dose-response curve. If concentrations are selected appropriately, the results of the method can be expressed as the concentration of the compound which is effective in inhibiting or promoting a certain percentage of mRNA expression for a specified gene. It is also preferred that blank wells, which contain cells and media but do not contain test compound, are included as controls. Positive controls, i.e., compounds which are known to either increase or decrease the mRNA expression, also may be included.

A wide variety of different types of potential anticancer agents may be tested in the method of this invention. For example, chemical agents, such as nucleoside analogs, biological agents such as peptides, proteins or antibodies, natural agents, such as extracts of plants, bacteria and fungi, and many other types of agents may be tested.

In a preferred method, once the desired cell density has been reached, the culture medium is removed from each well and is replaced with culture medium containing the test compound. Cultivation typically spans several days, and it is preferred that culture medium containing test compound be replaced on a periodic, e.g., daily, basis.

The present method permits the use of test compound concentrations in the micromolar range and below. The concentrations generally range from about 1 nanomolar to about 5 millimolar. Concentrations can be adjusted after initial results to obtain a useable dose-response curve.

After the cells have been cultivated in the presence of test compounds for a time sufficient for expression of target genes, the culture medium is removed and the cells of each well are analyzed by a quantitative nucleic acid application procedure. A nucleic acid sequence that is indicative of expression of the target gene is selected for amplification. The nucleic acid amplification technique may be any method that specifically amplifies the nucleic acid of interest, including polymerase chain reaction ("PCR"), ligase chain reaction ("LCR"), nucleic acid specific base amplification ("NASBA"), or Reverse Enzyme Activity DNA Interrogation Test ("READIT™") (Promega Corporation). PCR is the preferred amplification procedure.

The primers used for the amplification are selected so as to amplify a unique segment of the gene of interest. The amplification primers generally comprise from 8 to about 50, preferably from about 10 to 30 nucleotides. The primers are chosen to amplify a segment containing from about 25 to about 500, preferably from about 50 to about 150 nucleotides. Advantageously, the primers are selected such that the primer template complex has a melting point of about 50° C. Software that assists in primer design is commercially available.

The quantitative nucleic acid amplification technique is preferably a technique which involves monitoring the progress of the nucleic acid amplifications by use of an oligonucleotide probe having a fluorescent reporter molecule and a quencher molecule at either end. The quencher molecule substantially quenches any fluorescence from the reporter molecule when the oligonucleotide probe is intact, and the reporter is substantially unquenched whenever the oligonucleotide is digested by the exonuclease activity of the polymerase that is copying the template strand. This type of probe is sometimes referred to as a "TaqMan" probe. Quantitative PCR by this technique is described in U.S. Pat. No. 5,538,848 which issued on Jul. 23, 1996 to Livak et al., the disclosure of which is incorporated herein by reference. Related probes and quantitative amplification procedures are described in U.S. Pat. No. 5,716,784, which issued on Feb. 10, 1998 to Di Cesare et al. and U.S. Pat. No. 5,723,591, which issued on Mar. 3, 1998 to Livak et al., the disclosures of which are incorporated herein by reference. Instruments for carrying out quantitative PCR in microtiter plates are available from PE Applied Biosystems, 850 Lincoln Centre Drive, Foster City, Calif. 94404 under the trademark ABI Prism® 7700.

An alternative quantitative nucleic acid amplification procedure is described in U.S. Pat. No. 5,219,727, which issued on Jun. 15, 1993 to Wang et al., the disclosure of which is incorporated herein by reference. In this procedure, the amount of a target sequence in a sample is determined by simultaneously amplifying the target sequence and an internal standard nucleic acid segment. The amount of amplified DNA from each segment is determined and compared to a standard curve to determine the amount of the target nucleic acid segment that was present in the sample prior to amplification.

After determining the level of expression of the cancer gene in each microtiter well for a given compound, it is correlated to the concentration of the compound as an indicator of the compound's effectiveness in inhibiting or promoting the expression of the gene. If the range of concentrations is appropriate and a sufficient number of different concentrations is tested, a measure of the effectiveness can be calculated.

The method of this invention is further illustrated by the following examples, which is intended to illustrate and not limit the invention.

EXAMPLE 1

Cell Culture

Target cell lines are cultured in 96 well plates to 65–75% confluence in 100–150 μL of tissue culture media. Usually, cells are plated one to two days before treatment begins. The compound of interest is diluted in appropriate tissue culture media to various appropriate concentrations. 50–100 μL of these dilutions are then added to the cells in culture. Untreated cells and cells treated with known active compounds are included as controls. At various time points after the addition of the compound to the cells, the cells are lysed and total RNA is isolated using a Beckman Core System and a Biomek 2000 Liquid Handling System. This RNA is reverse transcribed using random hexamers as primers. The cDNA generated from this reaction is then subjected to real time PCR using primer/probe combinations that are specific for genes of interest utilizing a P/E Biosystems TaqMan 7700 sequence detection system. This system allows quantitation of the mRNA originally expressed in the treated cell lines.

Use of a select panel of cell lines of varying origin and analyzing expression of a number of different genes associated with oncogenesis, signal transduction, cell proliferation and/or cell death in response to treatment with known therapeutic agents will allow the establishment of a molecular database of molecular responsiveness. Compounds can then be analyzed for their effect on these cell lines and the data compared with the established expression database that has been generated using current conventional anti-cancer therapies. This comparison will allow one to identify and classify drug action and effectiveness and will aid in more accurately predicting the effect a drug will have in vivo.

EXAMPLE 2

Total RNA Isolation System Protocol

A method as described in the Promega SV Total RNA Isolation System Technical Manual (revised 12/98) is used.
1) Transfer 175 μL SV RNA lysis buffer (4 M guanidine thiocyanate, 0.01 M Tris (pH 7.5), 0.97%

β-mercaptoethanol) into 96 well plates containing cells (media must be removed prior to addition).
2) Pipet to mix and transfer to a 1 mL Bioblock
3) Add 350 μL of SV RNA Dilution Buffer and mix
4) Add 200 μL of 95% ethanol and mix
5) Transfer total volume to the clearing plate located on the binding plate all assembled on the vacuum manifold with solutions going to waste
6) Apply vacuum
7) Remove clearing plate
8) Add 900 μL SV RNA Wash Solution (60 mM potassium acetate, 10 mM Tris-HCl (pH 7.5 at 25° C.) and 60% ethanol)
9) Apply vacuum
10) Add 50 μL DNAse I to each well and incubate 15 minutes
11) Add 200 μL SV DNAse Stop Solution (2 M guanidine isothiocyanate, 4 mM Tris-HCl (pH 7.5) and 57% ethanol)
12) Apply vacuum
13) Add 900 μL SV RNA Wash Solution (60 mM potassium acetate, 10 mM Tris-HCl (pH 7.5 at 25° C.) and 60% ethanol)
14) Apply vacuum (continue vacuum for 1 minute after all the solution has passed through)
15) Place collection plate under binding plate
16) Add 100 μL RNAse free water
17) Apply vacuum
18) Save collection plate

EXAMPLE 3

Establishing a Database

Use of a select panel of cell lines of varying origin and analysis of the expression of a number of different genes associated with oncogenesis, signal transduction, cell proliferation and/or cell death in response to treatment with known therapeutic agents will allow a molecular database of molecular responsiveness to be established. Compounds can then be analyzed for their effect on these cell lines and the data compared with the established expression database that has been generated using current conventional anti-cancer therapies. This comparison will allow drug action and effectiveness to be identified thereby allowing more accurate prediction of the effect a drug will have in vivo.

What is claimed is:

1. A method for simultaneously screening a plurality of compounds for anti-cancer activity, which comprises the steps of:
    (a) cultivating cells, which serve as targets for anti-cancer agents in culture medium in wells of a microtiter plate, each well containing a culture volume of from about 50 μL to about 200 μL;
    (b) adding each compound being tested to individual cell-containing wells at at least one concentration at which the anti-cancer agent activity is to be tested;
    (c) culturing the cells for a time sufficient for the cells to express target genes;
    (d) lysing the cells to produce a cell lysate;
    (e) subjecting a sample of the cell lysate to quantitative nucleic acid amplification of a sequence from at least one target gene to directly measure the level of expression of the target gene in each well; and
    (f) comparing the target gene expression at different concentrations of compound to determine the effectiveness of each compound in altering cellular gene expression;
wherein each compound is selected for anti-cancer activity on the basis of inhibition of gene expression.

2. The method of claim 1, wherein each microtiter plate well contains less than about 100 ∞L of culture medium.

3. The method of claim 1 wherein, in step (a) the cells are cultivated until they are 65–75% confluent.

4. The method of claim 1, wherein each compound is tested at a plurality of different concentrations.

5. The method of claim 4, wherein one of said concentrations is zero.

6. The method of claim 1, wherein the level of expression of the target gene is measured by a Reverse Enzyme Activity DNA Interrogation Test.

7. The method of claim 1, wherein the quantitative nucleic acid amplification is quantitative polymerase chain reaction.

8. The method of claim 7, wherein the quantitative nucleic acid amplification further comprises an oligonucleotide probe which is complementary to the target gene segment being amplified and which has a fluorescent reporter molecule and a quencher molecule.

9. The method of claim 1, wherein at least one of steps (a)–(e) is robotically performed.

10. The method of claim 9 wherein steps (a)–(e) are robotically performed.

11. A method for simultaneously screening a plurality of compounds which affect expression of genes involved in apoptosis, tubulin polymerization, cell surface protein expression, signal transduction, cell proliferation, cell death or cytotoxicity, which comprises the steps of:
    (a) cultivating cells, which serve as targets for said compounds, in culture medium in wells of a microtiter plate, each well containing a culture volume of from about 50 μL to about 200 μL;
    (b) adding each compound being tested to individual cell-containing wells at a concentration at which activity of said compound is to be tested;
    (c) culturing the cells for a time sufficient for the cells to express target genes;
    (d) lysing the cells to produce a cell lysate;
    (e) subjecting a sample of the cell lysate to quantitative nucleic acid amplification of a sequence from at least one target gene to directly measure the level of expression of the target gene in each well and
    (f) comparing the target gone expression at different concentrations of compound to determine the effectiveness of each compound in altering cellular gene expression;
wherein each compound is selected for anti-cancer activity on the basis of inhibition of gene expression.

12. The method of claim 11, wherein each microtiter plate well contains less than about 100 μL of culture medium.

13. The method of claim 11, wherein in step (a) the cells are cultivated until they are 65–75% confluent.

14. The method of claim 11, wherein each compound is tested at a plurality of different concentrations.

15. The method of claim 14, wherein one of said concentrations is zero.

16. The method of claim 11, wherein the level of expression of the target gene is measured by a Reverse Enzyme Activity DNA Interrogation Test.

17. The method of claim 11, wherein the quantitative nucleic acid amplification is quantitative polymerase chain reaction.

18. The method of claim 17, wherein the quantitative nucleic acid amplification further comprises an oligonucleotide probe which is complementary to the target gene segment being amplified and which has a fluorescent reporter molecule and a quencher molecule.

19. The method of claim 11, wherein at least one of steps (a)–(e) is robotically performed.

20. The method of claim 19 wherein steps (a)–(e) are robotically performed.

21. A method for simultaneously screening a plurality of cell lines for the presence or absence of loss of heterozygosity or the presence or absence of a mutation, which comprises the steps of
   (a) cultivating cells, which serve as targets for said compounds in culture medium in wells of a microtiter plate, each well containing a culture volume of from about 50 $\mu$L to about 200 $\mu$L;
   (b) lysing the cells to produce a cell lysate;
   (c) subjecting a sample of the cell lysate to quantitative nucleic acid amplification of a sequence from at least one target gene directly measure the level of expression of the target gene in each well; and
   (d) comparing the amount of nucleic acid produced from said amplification, as measured by quantitative nucleic acid amplification, to the presence or absence of loss of heterozygosity or mutation.

22. The method of claim 21, wherein the level of expression of the target gene is measured by a Reverse Enzyme Activity DNA Interrogation Test.

23. The method of claim 21, wherein the quantitative nucleic acid amplification is quantitative polymerase chain reaction.

24. The method of claim 21, wherein the quantitative nucleic acid amplification further comprises an oligonucleotide probe which is complementary to the target gene segment being amplified and which has a fluorescent reporter molecule and a quencher molecule.

25. The method of claim 21, wherein at least one of steps (a)–(c) is robotically performed.

26. The method of claim 25 wherein steps (a)–(c) are robotically performed.

27. A method for preparing a database comprising the effects of compounds on expression of genes, which comprises the steps of:
   (a) cultivating cells, which serve as targets for said compounds, in culture medium in wells of a microtter plate, each well containing a culture volume of from about 50 $\mu$L to about 200 $\mu$L;
   (b) adding each compound being tested to individual cell-containing wells at a concentration at which activity of said compound is to be tested;
   (c) culturing the cells for a time sufficient for the cells to express target genes;
   (d) lysing the cells to produce a cell lysate;
   (e) subjecting a sample of the cell lysate to quantitative nucleic acid amplification of a sequence from at least one target gene to directly measure the level of expression of the target gene in each well;
   (f) detecting the level of gene expression determined by quantitative nucleic acid amplification for each compound; and
   (g) entering data obtained into a database which correlates each compound with its effect on gene expression for each target gene.

28. The method of claim 27 wherein said gene is involved in cancer, apoptosis, tubulin polymerization, cell surface protein expression, signal transduction, cell proliferation, cell death or cytotoxicity.

29. The method of claim 27, wherein each compound is tested at more than one concentration.

30. The method of claim 29, wherein one of said more than one concentration is zero.

31. The method of claim 27, wherein the level of expression of the target gene is measured by a Reverse Enzyme Activity DNA Interrogation Test.

32. The method of claim 27, wherein the quantitative nucleic acid amplification is quantitative polymerase chain reaction.

33. The method of claim 27, wherein the quantitative nucleic acid application further comprises an oligonucleotide probe which is complmentary to the target gene segment being amplified and which has a fluorescent reporter molecule and a quencher molecule.

34. The method of claim 27, wherein at least one of steps (a)–(e) is robotically performed.

35. The method of claim 34 wherein steps (a)–(e) are robotically performed.

* * * * *